United States Patent
Laviano et al.

(10) Patent No.: US 10,080,557 B1
(45) Date of Patent: Sep. 25, 2018

(54) SURGICAL INSTRUMENT (71) Applicant: Arthrex, Inc., Naples, FL (US)

(72) Inventors: Anthony A. Laviano, Fort Myers, FL (US); John P. Gualdoni, Naples, FL (US); Carl H. Wierks, Grandville, MI (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 15/992,704

(22) Filed: May 30, 2018

Related U.S. Application Data (62) Division of application No. 15/160,380, filed on May 20, 2016.

(51) Int. Cl.
*A61B 17/02* (2006.01)

(52) U.S. Cl.
CPC ........ *A61B 17/0218* (2013.01); *A61B 17/025* (2013.01); *A61B 2017/0275* (2013.01)

(58) Field of Classification Search
CPC .................... A61B 17/0218; A61B 17/025
See application file for complete search history.

(56) References Cited

U.S. PATENT DOCUMENTS

| | | | |
|---|---|---|---|
| 5,275,610 A | 1/1994 | Eberbach | |
| 5,454,365 A * | 10/1995 | Bonutti | A61B 17/0218 600/204 |
| 5,601,572 A | 2/1997 | Middleman | |
| 6,695,861 B1 | 2/2004 | Rosenberg et al. | |
| 8,206,291 B2 | 6/2012 | Fischvogt et al. | |
| 8,357,087 B2 | 1/2013 | Fetzer | |
| 8,617,167 B2 | 12/2013 | Weisel et al. | |
| 2005/0119685 A1 | 6/2005 | Smith | |
| 2009/0156903 A1 | 6/2009 | Guederian et al. | |
| 2011/0009705 A1 | 1/2011 | Bombard et al. | |
| 2011/0160538 A1 | 6/2011 | Ravikumar et al. | |
| 2011/0224742 A1 * | 9/2011 | Weisel | A61B 17/0218 606/86 R |
| 2011/0270295 A1 | 11/2011 | Litvack et al. | |
| 2012/0271357 A1 | 10/2012 | Arthur et al. | |
| 2014/0277038 A1 | 9/2014 | Goshayeshgar | |

OTHER PUBLICATIONS

MST Capsule Retractors, http://www.microsurgical.com/products/mst-capsule-retractors; 2 pages.
Freedom Ring, PMMA Capsular Tension Ring & PMMA Modified Capsular Tension Ring; http://www.freedomophthalmic.com/rinq.html; 2 pages.

* cited by examiner

*Primary Examiner* — Christian Sevilla
(74) *Attorney, Agent, or Firm* — Blank Rome LLP (57) ABSTRACT

A surgical instrument, such as a capsular retractor, and methods of use are disclosed.

8 Claims, 6 Drawing Sheets

SURGICAL INSTRUMENT

CROSS-REFERENCE TO RELATED APPLICATION

This is a divisional of U.S. patent application Ser. No. 15/160,380, filed May 20, 2016, the disclosure of which is incorporated by reference in its entirety herein.

BACKGROUND

Disclosed herein are methods and apparatus for surgical procedures. In particular, a surgical instrument, such as a capsular retractor, is disclosed herein and used to retract capsular tissue, and methods of accessing and retracting a joint capsule for better visualization during joint repair.

SUMMARY OF THE INVENTION

Surgical instruments, such as capsular retractors and cannula assemblies, according to exemplary embodiments, may comprise a cannulated shaft, a handle, a compression sleeve, one or more flexibly moveable members, such as retraction wings, and an actuating mechanism.

Further methods of arthroscopic surgery are disclosed. A method of retracting tissue of a joint may include inter alia: retracting tissue employing a surgical instrument, such as a capsular retractor having a cannulated shaft, a handle, a compression sleeve, one or more flexibly moveable members, and an actuating mechanism that deploys the one or more flexibly moveable members between inoperative and operative positions, to provide a surgical workspace with improved visualization of the repair. The tissue may be capsular tissue, such as hip capsule.

Other features and advantages will become apparent from the following description, which refers to the accompanying drawings.

DETAILED DESCRIPTION OF THE EXEMPLARY EMBODIMENTS

Surgical instruments, such as capsular retractors, and surgical techniques for endoscopic surgical repairs, for example, arthroscopic surgeries, are disclosed.

A surgical instrument according to an exemplary embodiment may be a capsular retractor that pulls a capsule away from the arthroscopic portals to allow for better visualization and to reduce interference of burrs and shavers for arthroscopic portals, thereby providing an improved surgical workspace. A capsule can be a capsule of the hip joint, humerus, knee, or the like. A capsular retractor may be a minimally invasive, percutaneous device that is used in the peripheral compartment during cam resection of hip arthroscopy, for example.

The surgical instrument may include a handle and a shaft attached to the handle. The shaft has a proximal end and a distal end. At least one flexibly movable member is positioned at the distal end of the shaft. The at least one flexibly movable member is movable between an operative position, in which the at least one flexibly movable member extends radially through an opening in the shaft in a direction substantially transverse to a longitudinal axis of the shaft, and an inoperative position, in which the at least one flexibly movable member extends substantially parallel to the longitudinal axis of the shaft. In an embodiment, the at least one flexibly movable member can be contained within the shaft when substantially parallel to the longitudinal axis in the inoperative position. An actuating mechanism is provided at the proximal end of the shaft. The actuating mechanism is configured to move the shaft in a first direction away from the handle and in a second direction toward the handle. Moving the shaft in the first direction extends the at least one flexibly movable member to the operative position and moving the shaft in the second direction retracts the at least one flexibly movable member to the inoperative position. In an embodiment, the surgical instrument includes a plurality of the flexibly movable members that are extended in the inoperative position and bent in the operative position.

A surgical instrument may include a handle, a cannulated shaft, a compression sleeve, at least one flexibly movable member, and an actuating mechanism, which may be similar in actuation to a retractable pen, for moving the flexibly movable member. A surgical instrument can also include a compression sleeve that is adjustable along the cannulated shaft and can be secured into grooves at desired locking locations. The at least one flexibly movable member can be located towards an end of the cannulated shaft and may be deployed and retracted with a simple press and release action of the actuating mechanism. When deployed, the at least one flexibly movable member prevents removal of the instrument. Pulling on the instrument after deployment of the flexibly movable member allows for dynamic retraction of the capsule. Static capsular retraction occurs once the compression sleeve is slid down to make firm contact with the patient's skin.

A surgical instrument may include an inner rod extending coaxially within an outer cylindrical sleeve, wherein the inner rod is slidably moveable relative to the outer cylindrical sleeve in a first direction away from the handle and a second direction toward the handle. The inner rod may be formed of nitinol, for example. The inner rod may be coupled with the one or more flexibly movable members located towards a distal end of the inner rod. Actuation of a press and release mechanism of the actuating mechanism (for example, a push button at a most proximal end of the inner rod) pushes the inner rod forward and causes the one or more flexibly movable members to bend and fold and to form wings on both sides of the outer cylindrical sleeve (i.e., the flexibly movable members move from the inoperative, non-folded, position to the operative position, folded or bent, position). In the operative position, the one or more flexibly movable members extend in a direction substantially transverse to a longitudinal axis of the inner rod and of the outer cylindrical sleeve. In the operative position, the one or more flexibly movable members extend in a direction substantially parallel to the longitudinal axis of the inner rod and of the outer cylindrical sleeve. The one or more flexibly movable members may be formed of nitinol, for example. A compression sleeve may be adjustable along the shaft and can be secured into grooves at desired locking locations.

Methods of conducting surgeries are also disclosed. A method may include the steps of inserting a distal end of the shaft of the surgical instrument into a joint through an incision made through a joint capsule; deploying the plurality of flexibly movable members on the shaft from an inoperative position in which the flexibly movable members extend substantially parallel to a longitudinal axis of the shaft to an operative position in which the flexibly movable members extend radially in a direction substantially transverse to the longitudinal axis of the shaft; engaging capsular tissue with the plurality of flexibly movable members; and drawing away the capsular tissue from the joint capsule to establish an improved surgical workspace.

A method of the present invention, such as arthroscopic surgery, may also include inter alia the steps of: (i) inserting a capsular retractor into a capsule (for example, a joint capsule), the capsular retractor comprising a handle, a cannulated shaft secured to and extending from the handle, a compression sleeve, flexibly movable members located towards a distal end of the cannulated shaft, and an actuating mechanism, the flexibly movable members being deployed (folded and/or bent) with a press and release action; (ii) deploying the flexibly moveably members; and (iii) retracting tissue with the capsular retractor.

Figure 14:
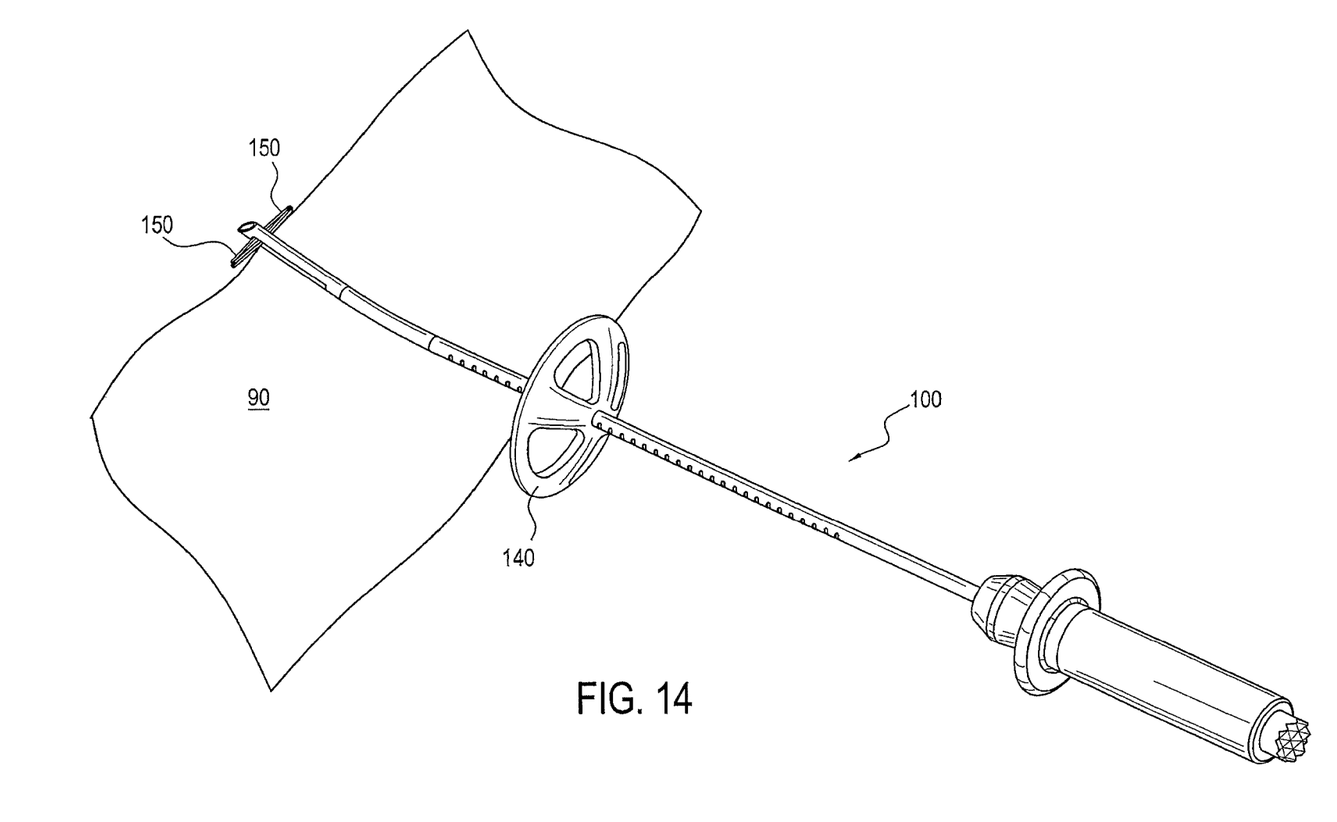
FIG. 14 illustrates the capsular retractor of FIG. 1 retracting tissue.

Referring now to the drawings, where like elements are designated by like reference numerals, FIGS. 1-13 illustrate exemplary embodiments of surgical instrument 100, 200. FIG. 14 illustrates the surgical instrument 100 retracting tissue 90.

Surgical instrument 100, such as a capsular retractor 100, illustrated in FIGS. 1-7 may comprise a handle 110, a cannulated shaft 120 secured to and extending from handle 110, a compression sleeve 140, one or more flexibly movable member 150, and an actuating mechanism 160. Cannulated shaft 120 may have an elongated outer sleeve body that defines a longitudinal axis 120a, a proximal end 122, and a distal end 124. Cannulated shaft 120 may be flexible or rigid, and may be formed of various materials, for example, metals such as stainless steel (in the shape of a stainless steel tubing), polymers, such as translucent polymer, or other known materials, alloys, or compositions known in the art. Cannulated shaft 120 may be in the form of an outer cylindrical sleeve. An inner rod 10 (shown in FIG. 7) connects actuating mechanism 160 with flexibly moveably members 150. Inner rod 10 of an actuating mechanism 160 may be formed of nitinol, for example. Flexibly movable members 150 may be formed of nitinol, for example.

The one or more flexibly movable members 150 may be positioned towards distal end 124 of cannulated shaft 120 and connected to actuating mechanism 160 by inner rod 10. As shown in exemplary embodiments of FIGS. 1-7, two flexibly movable members 150 may be provided. However, it is contemplated that any number of suitable flexibly movable members may be provided, for example one, two, three, four, five, or more. Each flexibly movable member 150 may have a proximal end 152 and a distal end 154. The flexibly movable members 150 may be affixed to cannulated shaft 120 near the proximal ends 152 or the distal ends 154 by any suitable means known in the art, for example, hingedly or pivotally affixed. In an embodiment where the flexibly movable members 150 are pivotally affixed to cannulated shaft 120, the flexibly movable members 150 may be affixed to cannulated shaft 120 at any point along the length of flexibly moveably members 150, for example at the proximal ends 152, the distal ends 154, or any point in between.

In one embodiment, the flexibly movable members 150 may be substantially transverse to the longitudinal axis 120a when deployed in the operative position. In other embodiments, the flexibly movable members 150 may be oriented after deployment in any suitable configuration and at any angle. For example, the flexibly movable members 150 may be configured to be deployed at 45 degrees relative to longitudinal axis 120a, any position between 45 degrees and 90 degrees, or any position greater than 0 degrees that permits suitable extension of the flexibly movable members 150. Each flexibly movable member 150 includes a foldable section 150a facilitating folding of the flexibly movable members 150 to the operative position.

Actuating mechanism 160 may be located in a portion of handle 110. Actuating mechanism 160 may be similar to a retractable pen. For example, a button 162 of the actuating mechanism 160 may be pressed down to deploy the flexibly movable members 150 in the operative position. Pressing and releasing button 162 once can secure flexibly movable members 150 in the operative position, and pressing and releasing button 162 again can retract flexibly movable members 150. In other embodiments, button 162 can be configured to deploy flexibly movable members 150 while button 162 is actively being depressed, and releasing button 162 will retract flexibly movable members 150. Other suitable mechanisms known in the art may also be employed.

Figure 5:
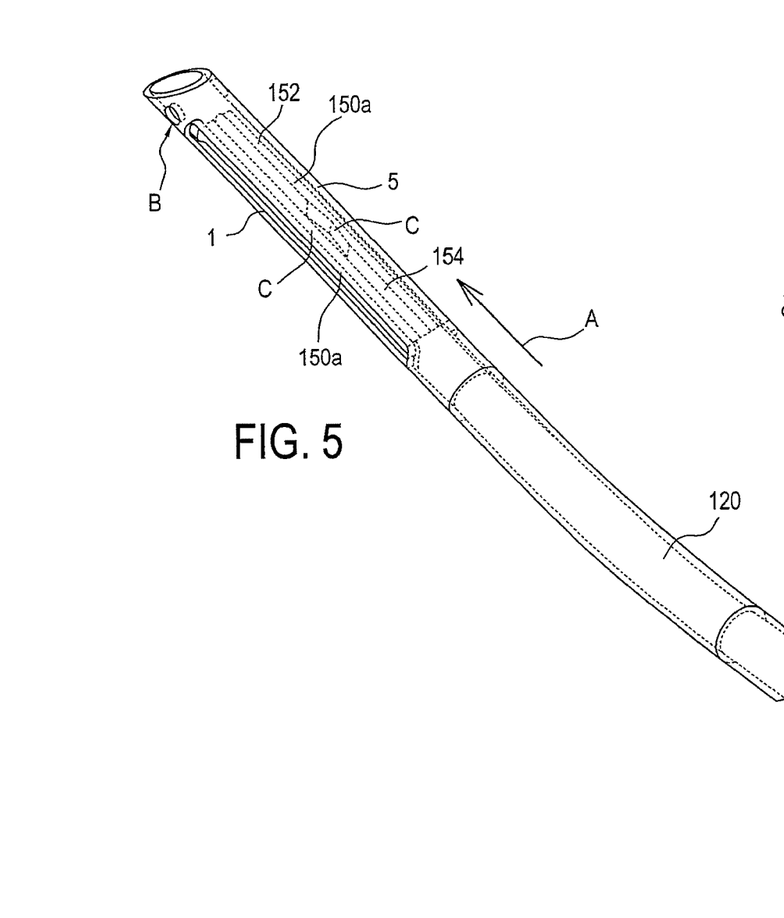
Figure 6:
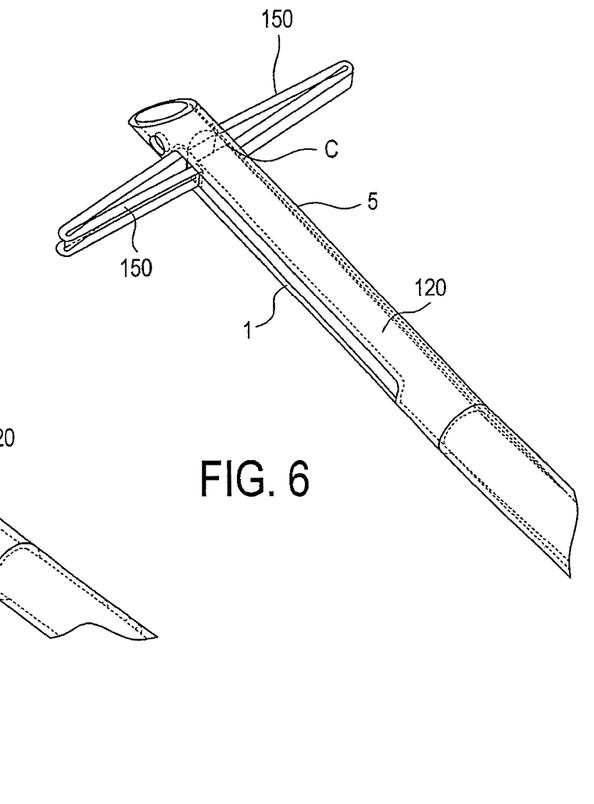
Figure 7:
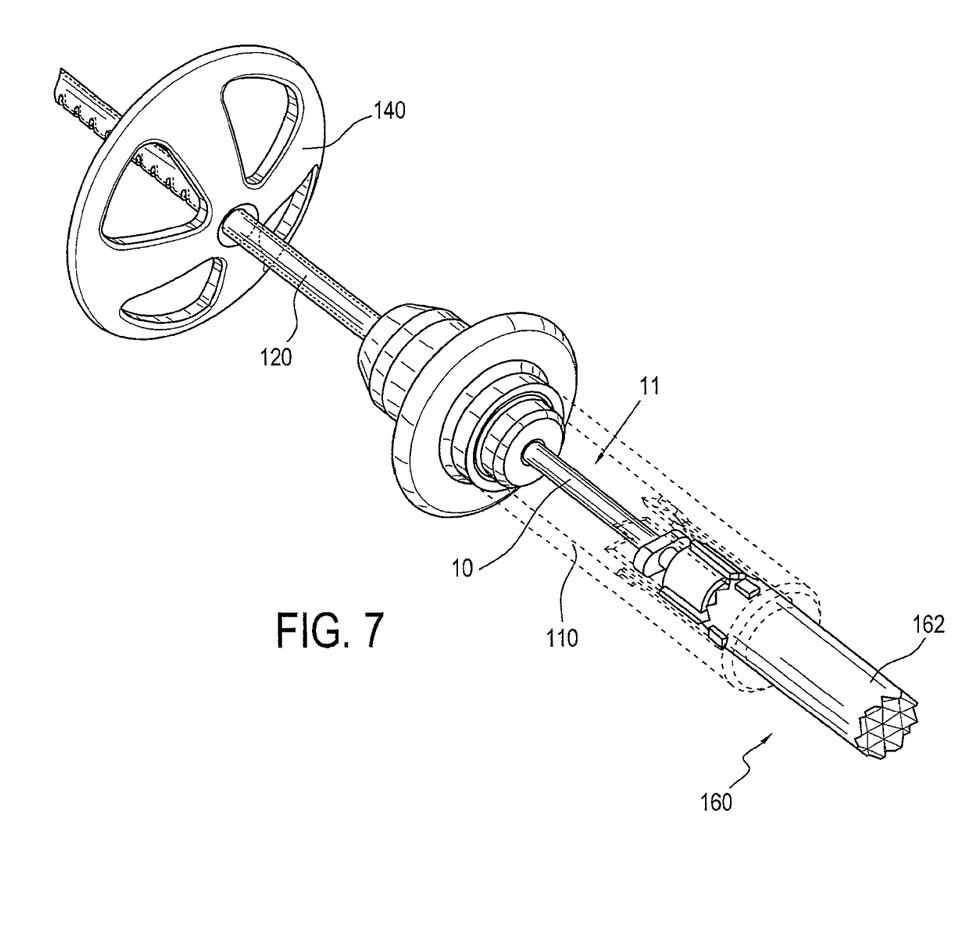
Figure 8:
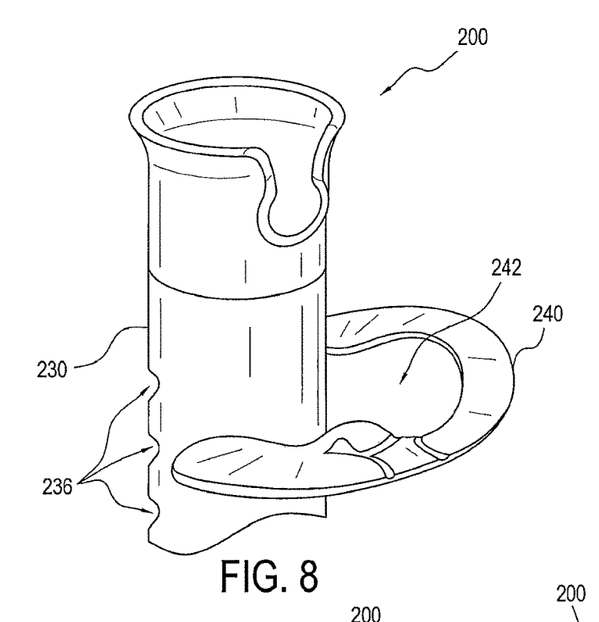
FIGS. 8-13 illustrate another surgical instrument, such as a capsular retractor, according to another exemplary embodiment.
Figure 9:
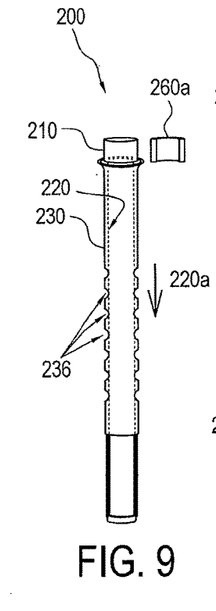

FIGS. 5-7 show details of actuating mechanism 160 and deployment of flexibly movable members 150. Actuating mechanism 160 (for example, a push button 162 at a most proximal end of the inner rod 10) pushes the inner rod 10 forward away from the handle 110 and causes flexibly movable members 150 to bend and fold to form wings on both sides of the outer cylindrical sleeve (i.e., the flexibly movable members 150 move from the inoperative (non-folded) position, as shown in FIG. 5; and retracts the inner rod 10 toward the handle 110 to move the flexibly movable members 150 to an operative position (folded or bent), as shown in FIG. 6. In the operative position, the flexibly movable members 150 extend in a direction substantially transverse to the longitudinal axis 120a of shaft 120. In the inoperative (non-folded) position, as shown in FIG. 5, the flexibly movable members 150 extend in a direction about parallel to the longitudinal axis 120a. Actuation of the press and release mechanism 160 cause the flexibly moveable members 150 to return to the inoperative position.

Figure 1:
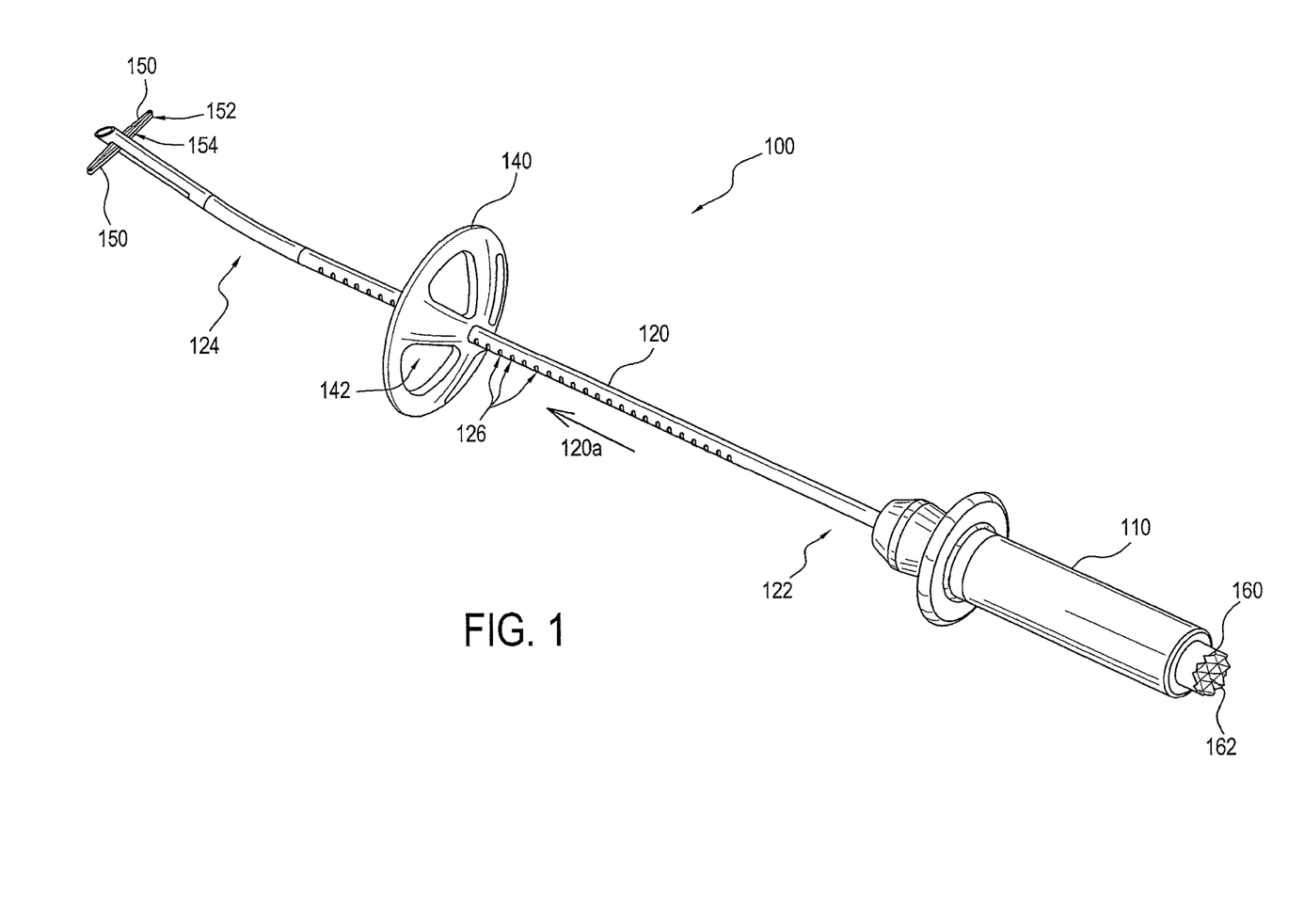
FIGS. 1-7 illustrate a surgical instrument, such as a capsular retractor, according to an exemplary embodiment.
Figure 2:
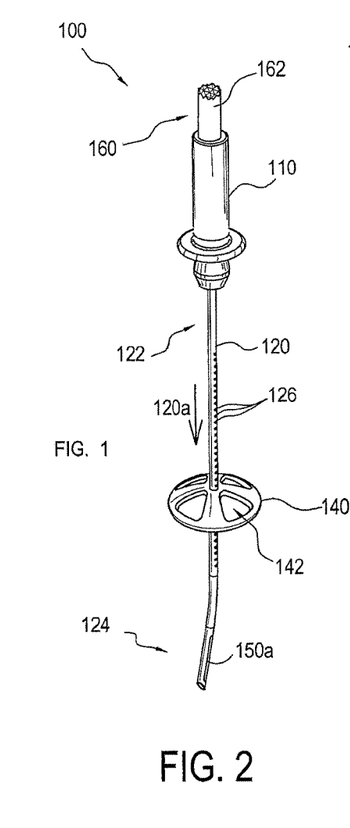
Figure 3:
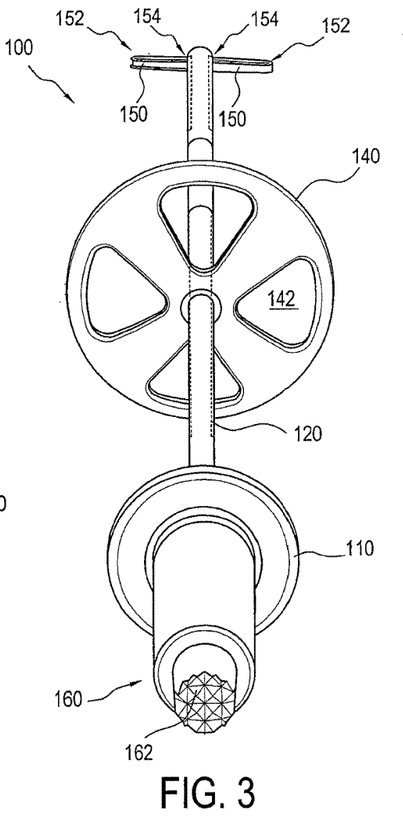
Figure 4:
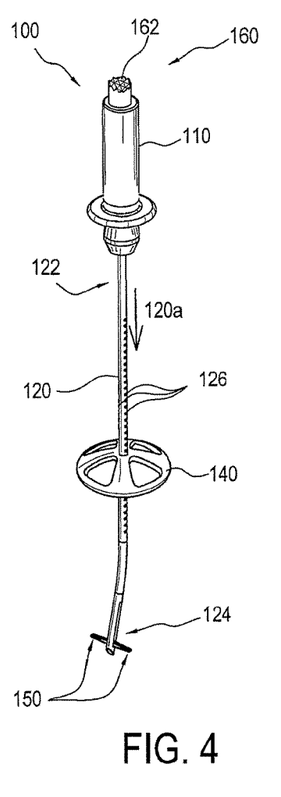

FIGS. 5 and 6 are enlarged views of a proximal end of the surgical instrument 100 of FIG. 1 illustrating how pushing forward on the shaft in the direction away from the handle 110 (direction A) causes the flexibly movable members 150 to bend and fold and to form wings. As illustrated in FIG. 5, flexibly movable members 150 are securely attached to shaft 120, for example, pinned at location B at a most distal end of the cylindrical shaft 120. Folding of flexibly movable members 150 may occur at about half the length of the flexibly movable members, for example, at location C shown in FIGS. 5 and 6.

In the operative (folded or bent) position, the flexibly movable members 150 extend in a direction generally transverse to longitudinal axis 120a of the outer cylindrical sleeve 120 and inner rod 10. Flexibly movable members 150 may be in the shape of distal radially expanding members or fingers that are designed and shaped to pass through corresponding openings 1 and 5 on a distal portion of the outer cylindrical sleeve 120. Thereby, when actuated to be in the operative position, the at least one flexibly movable member 150 will extend radially through the opening 1 or 5. Flexibly movable members 150 may also have a flower-type or mushroom-type arrangement when in the operative, folded or bent, position.

FIG. 7 is an enlarged view of a distal end of the surgical instrument 100 of FIG. 1 illustrating how compressing button 162 of the actuating mechanism 160 (press and release mechanism 160) pushes the rod and shaft forward in the direction A and causes the flexibly movable members 150 to bend and fold to form wings. A spring 11 may be located within rod 10, as shown in FIG. 7, to facilitate pushing of the shaft forward relative to the handle 110.

Compression sleeve 140 may comprise one or more protuberances configured to correspond with grooves 126 in locking positions on shaft 120 to secure compression sleeve 140 into place. Shaft 120 may include other suitable locking mechanisms to secure compression sleeve 140 into place. For example, shaft 120 may include holes or screw-like threads instead of grooves 126. Compression sleeve 140 may include a thumb screw that can be tightened to secure compression sleeve 140 in a desired position along shaft 120, a retractable pin, or the like. A thumb screw or a retractable pin can be configured to mate with grooves 126 or holes on cannulated shaft 120. In an embodiment, compression sleeve 140 can be threaded to correspond with a screw-like thread on cannulated shaft 120, so that the position of compression sleeve 140 can be changed by screwing or unscrewing compression sleeve 140 along cannulated shaft 120. Any other means known in the art may also be used to permit compression sleeve 140 to be slidably positioned along longitudinal axis 120*a* and temporarily secured on cannulated shaft 120.

Compression sleeve 140 can be formed of any suitable material known in the art. Compression sleeve 140 can be solid, or can have gaps 142, as depicted in FIGS. 1-4. Grooves 126, or alternatively holes or screw-like threads, may be provided on the whole length of shaft 120 at locking locations, or on at least a length of shaft 120.

FIGS. 8-13 illustrate various views of a surgical instrument 200 according to another exemplary embodiment. Surgical instrument 200 may include a handle 210, an inner tube 220 that is adapted to cooperate with a corresponding outer cylindrical sleeve 230, a compression sleeve 240, and at least one flexibly movable member 250.

Inner tube 220 may be secured to and extend from handle 210, and may be slidably moveable relative to outer cylindrical sleeve 230 along a longitudinal axis 220*a*. Inner tube 220 can have a first diameter and outer cylindrical sleeve 230 can have a second diameter, the first diameter being smaller than the second diameter. Inner tube 220 may have a proximal end 222 and a distal end 224, and outer cylindrical sleeve 230 may have a proximal end 232 and a distal end 234. Inner tube 220 and outer cylindrical sleeve 230 can extend along a longitudinal axis 220*a*. Inner tube 220 and outer cylindrical sleeve 230 can be flexible or rigid, and may be formed of various materials, for example, metals such as stainless steel (in the shape of a stainless steel tubing), polymers such as translucent polymer, or other known materials, alloys, or compositions. Inner tube 220 may be formed of nitinol or similar material(s).

At least one flexibly movable member 250 can be positioned towards distal end 224 of inner tube 220 or distal end 234 of outer cylindrical sleeve 230. Flexibly movable members 250 can be affixed to inner tube 220 or outer cylindrical sleeve 230 along longitudinal axis 220*a*. As shown in exemplary embodiments of FIGS. 10 and 11, two flexibly movable members 250 may be provided. However, it is contemplated that any number of flexibly movable members 250 may be provided, for example one, two, three, four, five, or more. Each flexibly movable member 250 can have a proximal end 252 and a distal end 254. Flexibly movable members 250 may be affixed to inner tube 220 or outer cylindrical sleeve 230 near proximal end 252 or distal end 254 by any suitable means known in the art, for example, hingedly or pivotally affixed. In an embodiment where flexibly movable members 250 are pivotally affixed to inner tube 220 or outer cylindrical sleeve 230, flexibly movable members 250 can be affixed to inner tube 220 or outer cylindrical sleeve 230 at any point along the length of flexibly movable members 250, for example at proximal end 252, distal end 254, or any point in between.

Figure 10:
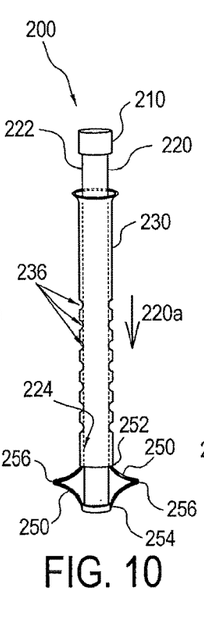
Figure 11:
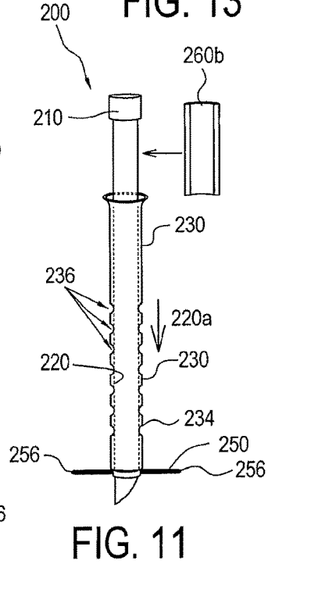
Figure 12:
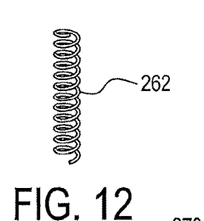
Figure 13:
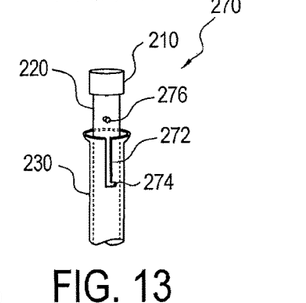

Flexibly movable members 250 can further be configured to have a hinge 256 near a midpoint of the respective flexibly movable members 250 such that deployment of flexibly movable members 250 results in hinge 256 extending outward from longitudinal axis 220*a* and proximal ends 252 and distal ends 254 of flexibly movable members 250 are drawn towards each other, as shown in an exemplary embodiment in FIGS. 10 and 11.

Flexibly movable members 250 can be deployed by retracting inner tube 220. Flexibly movable members 250 can be deployed by pushing forward inner tube 220. Flexibly movable members 250 can be secured in a deployed position by placing a removable spacer 260*a*, 260*b* around a portion of inner tube 220 that extends out from cylindrical sleeve 230, thus holding inner tube 220 in a retracted position. Flexibly movable members 250 can be secured in a deployed position by a biasing spring 262 configured to bias inner tube 220 in an extended position. Flexibly movable members 250 can be secured in a deployed position by a tongue-in-groove configuration 270 as illustrated in FIG. 10. Tongue-in-groove configuration 270 can comprise a slot 272 in outer cylindrical sleeve 230, a notch 274 at an end of slot 272, and a pin 276 on inner tube 220. In an example tongue-in-groove embodiment, tongue-in-groove configuration 270 can be configured to deploy flexibly movable members 250 when inner tube 220 is pressed down and turned such that pin 276 enters slot 272, continues to the end of slot 272, and is then positioned in notch 274. In another tongue-in-groove embodiment, tongue-in-groove configuration 270 can be configured to retain flexibly movable members 250 in a retracted state when pin 276 is positioned in notch 274, and then deploy flexibly movable members 250 when inner tube 220 is turned and retracted from outer cylindrical sleeve 230 such that pin 276 exits notch 274, travels up slot 272, and then exits slot 272.

Flexibly movable members 250 may be oriented at an angle with the inner tube 220 and the outer cylindrical sleeve 230. Flexibly movable members 250 can be oriented approximately 90 degrees to longitudinal axis 220*a* when deployed. In other embodiments, flexibly movable members 250 may be oriented after deployment in any suitable configuration known in the art. For example, flexibly movable members 250 may be configured to be deployed at 45 degrees relative to longitudinal axis 220*a*, any position between 45 degrees and 90 degrees, or any position greater than 0 degrees that permits suitable extension of flexibly moveably members 250.

Compression sleeve 240 may include at least one protrusion configured to correspond with grooves 236 positioned on outer cylindrical sleeve 240 to secure compression sleeve 240 into place. Outer cylindrical sleeve 240 may include other suitable locking mechanisms to secure compression sleeve 240 into place. For example, outer cylindrical sleeve 230 may include holes or a screw-like thread instead of grooves 236. Compression sleeve 240 may include a thumb screw that can be tightened to secure compression sleeve 240 in a desired locking position along outer cylindrical sleeve 230, a retractable pin that can be inserted into a corresponding mating element of outer cylindrical sleeve 230, or the like. A thumb screw or a retractable pin can be configured to mate with grooves 236 or holes on outer cylindrical sleeve 230. In an embodiment, compression sleeve 240 may be threaded to correspond with a screw-like thread on outer cylindrical sleeve 230, so that the position of compression sleeve 240 can be changed by screwing or unscrewing compression sleeve 240 along outer cylindrical sleeve 230. Any other means known in the art may also be used to permit compression sleeve 240 to be slidably positioned along longitudinal axis 220a and temporarily secured on outer cylindrical sleeve 230.

Compression sleeve 240 may be formed of any suitable material known in the art. Compression sleeve 240 may be solid, or may have gaps 242, as depicted in FIG. 5. Grooves 236, or alternatively holes or screw-like threads, may be provided on the whole length of outer cylindrical sleeve 230, or on at least a length of outer cylindrical sleeve 230.

FIG. 14 illustrates surgical instrument 100 retracting tissue 90. Surgical instrument retractor 100, 200 can penetrate through an incision to a target tissue desired to be retracted. Target tissue 90 can be, for example, a hip capsule. However, surgical instrument 100, 200 may be utilized to penetrate and retract other tissues as well. After penetrating the desired target tissue, flexibly movable members 150, 250 may be deployed as described above.

Compression sleeve 140, 240 may then be slidably positioned along longitudinal axis 110a, 220a and moved into contact with an outer surface of the patient's skin. The compressive sleeve is designed to counteract the retracting force of the flexibly movable members 150, 250 at the level of the skin, and adjusts in position to hold the instrument in place, effectively squeezing the tissue between the skin and capsule. Because the surgical instrument will be placed from a distal position, the compression sleeve may sit on an angle, tilted towards the angle of the tip of the instrument. In one embodiment, the cutout for the central hole in the compression sleeve that receives the shaft could be made at 45 degree angle with respect to the shaft to accommodate the tilt. Compression sleeve 140, 240 can be secured into place by any means described above, for example, a groove/protrusion design, thumb screw, retractable pin, screw and thread, or any other means known in the art.

Surgical instrument 100, 200 can then be drawn back and away from the penetrated tissue. Flexibly movable members 150, 250 contact an inner surface of the penetrated tissue, thereby retracting the penetrated tissue when surgical instrument 100, 200 is drawn back.

After the penetrated tissue no longer needs to be retracted, compression sleeve 140, 240 can be slidably moved away from the outer surface of the patient's skin. Flexibly movable members 150, 250 can be retracted as described in any of the embodiments described above. Surgical instrument 100, 200 can then be removed from the penetrated tissue.

Although surgical instrument 100, 200 may be used in cavities, such as joints (i.e., hips, knees, shoulders, elbows, ankles, and the like), it can also be used in large body cavities, such as the abdomen. Employing surgical instrument 100, 200 in surgeries, such as arthroscopic surgeries, provides an efficient and simple method of retracting tissue and creating an improved surgical workspace.

A method of the present invention may include the steps of inserting a distal end 124, 224 of the shaft 120, 220 of the surgical instrument 100, 200 into a joint through an incision made through a joint capsule; deploying the plurality of flexibly movable members 150, 250 on the shaft from an inoperative position in which the flexibly movable members extend substantially parallel to a longitudinal axis 120a, 220a of the shaft to an operative position in which the flexibly movable members extend radially in a direction substantially transverse to the longitudinal axis of the shaft; and engaging capsular tissue with the plurality of flexibly movable members and drawing away the capsular tissue from the joint capsule to establish an improved surgical workspace.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention.

What is claimed is:

1. A method of retracting capsular tissue of a joint to provide a surgical workspace, comprising:
  inserting a distal end of a shaft of a surgical instrument into a joint through an incision made through a joint capsule;
  deploying at least one flexibly movable member positioned at the distal end of the shaft from an inoperative, position in which the flexibly movable member extends substantially parallel to a longitudinal axis of the shaft to an operative position in which the flexibly movable member extends radially in a direction substantially transverse to the longitudinal axis of the shaft;
  engaging capsular tissue with the flexibly movable member and drawing away the capsular tissue from the joint capsule to provide the surgical workspace; and
  folding the flexibly moveable member when deploying the flexibly moveable member to the operative position.

2. The method of claim 1, further comprising pressing a button of an actuating mechanism of the surgical instrument to deploy the flexibly moveable member from the inoperative position to the operative position.

3. The method of claim 1, further comprising moving the shaft of the surgical instrument in a direction away from a handle to deploy the flexibly moveable member from the inoperative position to the operative position.

4. The method of claim 1, wherein the capsular tissue is hip capsular tissue.

5. A method of retracting capsular tissue of a joint to provide a surgical workspace, comprising:
  inserting a distal end of a shaft of a surgical instrument into a joint through an incision made through a joint capsule;
  deploying at least one flexibly movable member positioned at the distal end of the shaft from an inoperative position in which the flexibly movable member extends substantially parallel to a longitudinal axis of the shaft to an operative position in which the flexibly movable member extends radially in a direction substantially transverse to the longitudinal axis of the shaft;
  engaging capsular tissue with the flexibly movable member and drawing away the capsular tissue from the joint capsule to provide the surgical workspace; and
  pressing a button of an actuating mechanism of the surgical instrument to deploy the flexibly moveable, member from the inoperative position to the operative position.

6. The method of claim 5, further comprising folding the flexibly moveable member when deploying the flexibly moveable member to the operative position.

7. The method of claim 5, further comprising moving the shaft of the surgical instrument in a direction away from a handle to deploy the flexibly moveable member from the inoperative position to the operative position.

8. The method of claim 5, wherein the capsular tissue is hip capsular tissue.

\* \* \* \* \*